United States Patent [19]

Issaq

[11] 4,430,217
[45] Feb. 7, 1984

[54] ANTI-RADIAL CHROMATOGRAPHY DEVICE

[75] Inventor: Haleem J. Issaq, Frederick, Md.

[73] Assignee: Litton Bionetics, Inc., Kensington, Md.

[21] Appl. No.: 264,751

[22] Filed: May 18, 1981

[51] Int. Cl.³ .............................................. B01D 15/08
[52] U.S. Cl. ..................................... 210/198.3; 422/70
[58] Field of Search ......................... 210/198.3; 422/70

[56] References Cited

U.S. PATENT DOCUMENTS

| | | | |
|---|---|---|---|
| 3,265,214 | 8/1966 | Brodsky | 210/198.3 |
| 3,295,683 | 1/1967 | Litt et al. | 210/198.3 |
| 3,491,883 | 1/1970 | Schriftmon | 210/198.3 |
| 3,928,203 | 12/1975 | Kremer | 210/198.3 |
| 4,272,381 | 1/1981 | Kremer | 210/198.3 |

*Primary Examiner*—John Adee
*Attorney, Agent, or Firm*—Robert A. Seldon

[57] ABSTRACT

An anti-radial chromatographic device is disclosed preferably comprising an inner Petri dish nested concentrically within an outer Petri dish of slightly larger diameter. The bottom surface of the inner dish is spaced from the bottom surface of the outer dish to form a solvent-containing chamber. A annular wick contained in the annular space between the two dishes extends above the tops of the dishes and conducts the solvent upward to the lower surface of a downward-facing chromatographic plate resting on the wick.

1 Claim, 2 Drawing Figures

ANTI-RADIAL CHROMATOGRAPHY DEVICE

BACKGROUND OF THE INVENTION

The present invention relates to the technique of anti-radial chromatography. In the general method, a planar chromatographic medium, such as a thin layer chromatography plate, is employed. Samples are spotted on the periphery of a circle and eluant is applied at the outer edge of the circle. Elution is therefore radial, the solvent front advancing inwardly from the circumference of the circle toward the center. The method is extremely efficient and allows the separation of up to 50 samples on a 10 cm × 10 cm plate in five minutes, using 5 ml of solvent. If a 20 cm × 20 cm plate is used, up to 120 samples can be analyzed simultaneously. The technique is useful in almost every analytical laboratory where separations are carried out. The method is applicable in clinical, pharmaceutical, environmental, agricultural, forensic and quality control laboratories.

Successful application of the method depends especially upon the uniform radial advance of the solvent front toward the center of the circle. Best results are achieved by ensuring uniform application of the eluting solvent and prevention of gravitational effects, air currents and the like during elution.

Prior art devices for carrying out anti-radial high performance thin layer chromatography have been described by Kaiser, R. E., *High Resolution Chromatography and Chromatographic Communications*, 1, 164 (1978), and by Kariko, K., et al, Ibid, 2, 247 (1979). The device of the present invention offers advantages of greater simplicity of design and construction, reduced expense and better control of process variables during elution.

SUMMARY OF THE INVENTION

Accordingly, an anti-radial chromatography device is provided which comprises an inner generally cylindrical dish nested within an outer generally cylindrical dish of slightly larger diameter to form a first chamber between the bottoms of the dishes as well as a space between the side walls in communication with the first chamber. Capillary transport means between the side walls extends between the chamber to a region above the tops of the side walls to transfer fluid from the first chamber.

A chromatography plate contacts the capillary transport means and forms a second solvent chamber with the inner dish.

DETAILED DESCRIPTION OF THE INVENTION

The apparatus of the present invention has as its principal components two shallow flat-bottomed dishes arranged concentrically. The material of the dishes should be inert to the wide variety of solvents employed in thin-layer chromatography. Suitable materials may be glass, metal, ceramic and plastics. However, the preferred material is glass, and the apparatus can be constructed, for example, using glass Petri dishes. The diameter of the outer dish is determined by the size of the chromatograph plate to be employed. The diameter of the inner dish is chosen such that, when the dishes are nested concentrically, an annular space between the side walls of between about 0.2 mm to 3.0 mm is maintained.

Figure 1:
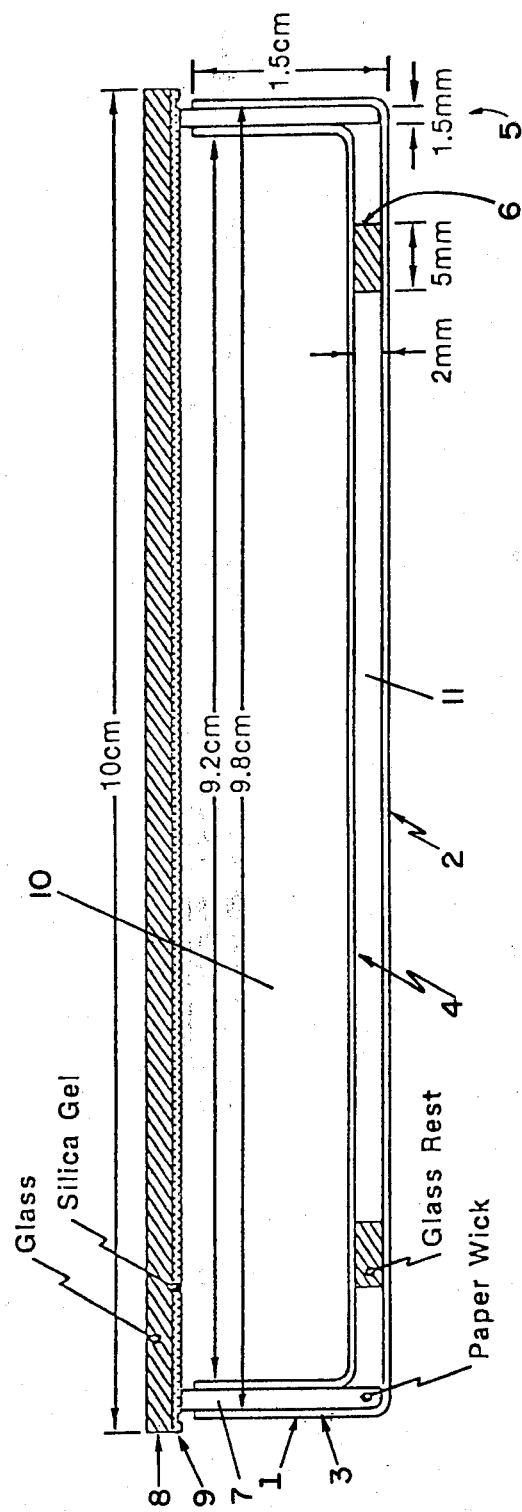
FIG. 1 is a cross-sectional view of the chromatography chamber with a thin-layer chromatography plate mounted thereon.

FIG. 1 is a cross-sectional view of a preferred embodiment of the anticircular chromatography chamber assembly. The outer dish 1 is conveniently constructed of a glass Petri dish, 9.8 cm inner diameter, to accommodate a commercially available thin-layer chromatography plate 8 positioned with the silica layer 9 down, as shown. The outer dish 1 has an essentially flat bottom 2 and a vertical cylindrical side well 3, extending in a preferred embodiment 1.5 cm in height. Nested concentrically within the outer dish is an inner dish 4, essentially congruent with the outer dish, having a 9.2 cm inner diameter. Accordingly, a 1.5 mm space 5 is between the side walls of the inner and outer dishes.

Capillary transport means, preferably a circumferential paper wick 7, is held tightly in place between the two side walls. The dimensions of the gap and thickness of the wick must be correlated to ensure that the wick is held firmly in place between the dishes. For a gap between the side walls of 1.5 cm, and paper wick 16 mm wide by 1.5 mm thick is inserted in the gap. The wick 7 surrounds the entire circumference of the inner dish.

The bottoms of the inner and outer dishes are separated by spacers 6, also of an inert material, preferably glass, of uniform dimension, thereby forming, between the inner and outer dishes, an outer solvent chamber 11. The dimensions of the spacer 6 are such as to provide about a 2 mm deep outer solvent chamber 11, and to render the top edges of the inner and outer side walls flush. The developing solvent is placed in the outer solvent chamber 11, conducted upwardly through the wick 7 to the surface of a chromatography plate 8 which is placed face down over the apparatus. The plate 8 rests on the wick 7, which extends above the tops of the dish side walls slightly. When the chromatography plate 8 is in place, it forms a lid enclosing an inner chamber 10.

In the preferred embodiment, 10 ml of eluting solvent is placed in the outer solvent dish.

When a 10 cm × 10 cm thin-layer plate is used in conjunction with the preferred embodiment of the invention, a circle 10 cm in diameter is first scored on the plate with a sharp spatula. The sample is spotted on the plate at a distance of 5 mm inside the scored circle. The plate is placed absorbent side down, resting on the paper wick which abuts the plate between the groove and the sample.

When the plate is positioned on the apparatus, a second, inner solvent chamber is formed. The inner solvent chamber is a unique feature of the apparatus of the present invention. Solvent, or conditioning reagents, may be placed in the inner solvent chamber. This feature makes it possible to control the atmosphere in which chromatographic development takes place. The use of eluting solvent in the outer solvent chamber permits development of the chromatogram in a solvent-saturated atmosphere. Furthermore, the inner solvent chamber permits the use of conditioning agents during development, for example, sulfuric acid to control humidity, or ammonia to control streaking. If desired, the inner solvent chamber may be so constructed to provide a number of non-interconnected wells for keeping several such materials separately in the inner chamber.

Figure 2:
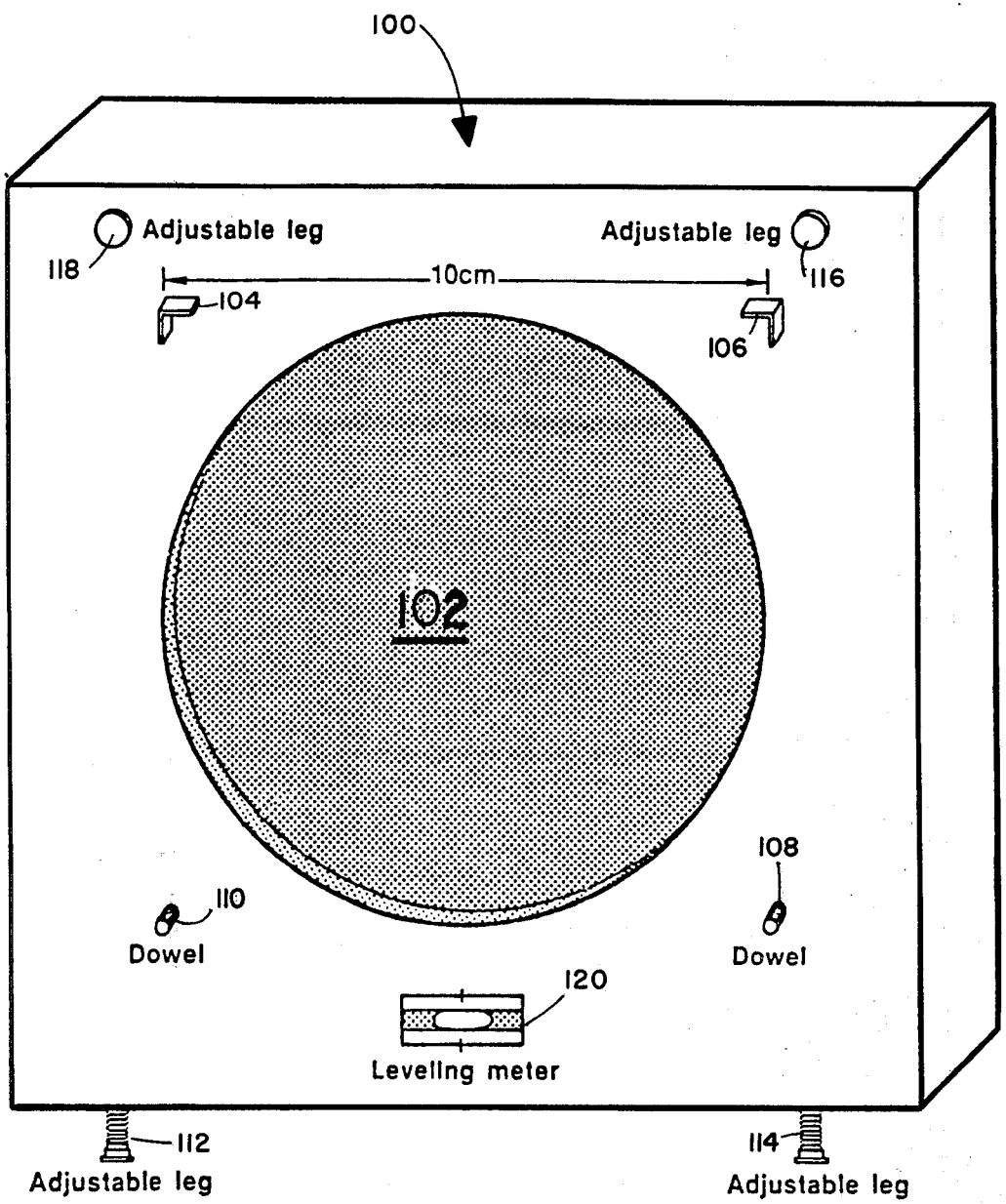
FIG. 2 is a plan view of a holder for the chromatographic chamber adapted for centering and leveling the chamber prior to use.

To ensure an even flow of the solvent, the chromatography chamber just described is placed on a special platform 100 (FIG. 2) having adjustable legs 112, 114, 116, 118 and a horizontal leveling meter 120. The platform serves for centering and leveling the chromatography chamber and for reproducibly positioning the chromatography plate. A circular recess, 102 into which the outside dish fits, serves to center the apparatus. In the preferred embodiment, the recess is 3 mm deep and 10 cm in diameter. The platform is equipped with two corner pieces, 104, 106 opposite of which, positioned to form a square array, two dowels are situated. The corner pieces and the dowels ensure exact positioning of the chromatography plate. In the preferred embodiment, the corner pieces are 10 cm apart on one side of the square, and the dowels 108, 110 are positioned at a distance 10 cm from the corner pieces and from each other.

During development of the chromatogram, the entire apparatus is maintained in a totally enclosed chamber or cover to eliminate drafts. Between the runs, the chromatographic chamber is covered with a dish having the same dimensions as the outside dish, to retain the saturated atmosphere and prevent evaporative loss of solvents.

What is claimed is:

1. An anti-radial chromatographic device comprising a shallow outer dish having an essentially flat bottom and a vertical cylindrical side well, opening upwardly an inner dish in form essentially congruent with the outer dish and nesting concentrically within the outer dish providing a uniform clearance of 0.2 mm to 3.0 mm between the inner and outer vertical side walls, spacing means separating the bottoms of the inner and outer dishes and forming an outer solvent chamber therebetween, capillary transport means between the inner and outer side walls and extending slightly beyond the tops of said walls for transferring fluid upwardly from the outer dish solvent chamber, the outer dish resting upon a platform having leveling and centering means for leveling and centering the outer dish, and a chromatography plate covering the inner and outer plates and contacting the capillary transport means, thereby forming an inner solvent chamber bounded by the inner dish and the chromatographic plate.

* * * * *